(12) United States Patent
Vries et al.

(10) Patent No.: US 6,294,680 B1
(45) Date of Patent: Sep. 25, 2001

(54) PROCESS FOR THE PRODUCTION OF SEMI SYNTHETIC STATINS VIA NOVEL INTERMEDIATES

(75) Inventors: Ton Rene Vries; Hans Wijnberg; Wijnand Sjourd Faber, all of Groningen; Venetka Ivanova Kalkman-Agayn, Den Haag; Mieke Ivanova Sibeyn, Amersfoort, all of (NL)

(73) Assignee: Plus Chemicals, B.V., Mijdrecht (NL)

( * ) Notice: Subject to any disclaimer, the term of this patent is extended or adjusted under 35 U.S.C. 154(b) by 0 days.

(21) Appl. No.: 09/341,809

(22) PCT Filed: Jan. 27, 1998

(86) PCT No.: PCT/EP98/00519

§ 371 Date: Jan. 5, 2000

§ 102(e) Date: Jan. 5, 2000

(87) PCT Pub. No.: WO98/32751

PCT Pub. Date: Jul. 30, 1998

(30) Foreign Application Priority Data

Jan. 28, 1997 (EP) .................................................. 97200223
Sep. 3, 1997 (EP) .................................................. 97306809

(51) Int. Cl.⁷ ........................ C07D 319/06; C07D 411/00
(52) U.S. Cl. ........................... 549/373; 549/292; 549/18; 546/207; 548/405; 548/413; 548/517; 548/527; 560/55; 560/179; 560/226; 558/85; 558/86

(58) Field of Search ............................... 549/373, 18, 292; 546/207; 548/405, 413, 517, 527; 558/85, 86; 560/55, 179, 226

(56) References Cited

U.S. PATENT DOCUMENTS 6,100,407   8/2000   Van Dalen et al. ................. 549/373

FOREIGN PATENT DOCUMENTS

| 0 299 656 | 1/1989 | (EP) . |
| 0 415 488 | 3/1991 | (EP) . |
| 0 940 395 | 9/1999 | (EP) . |
| 95 13283 | 5/1995 | (WO) . |

OTHER PUBLICATIONS

Askin D et al.: "Synthesis of Synvinolin: Extremely High Conversion Alkylation of an Ester Enolate" Journal of Organic Chemistry, vol. 56, No. 16, Aug. 1991, pp. 4929–4932, XP000676448.

*Primary Examiner*—Amelia Owens
(74) *Attorney, Agent, or Firm*—Kenyon & Kenyon

(57) ABSTRACT

A process has been provided to produce semi synthetic statins, as for instance simvastatin with a high yield, for another statin, preferably a naturally occurring statin, as for instance lovastatin. Also a number of novel intermediate compounds, prepared during said process, has been provided.

41 Claims, 2 Drawing Sheets

PROCESS FOR THE PRODUCTION OF SEMI SYNTHETIC STATINS VIA NOVEL INTERMEDIATES

BACKGROUND OF THE INVENTION

The present invention relates to a process for preparing semi-synthetic statins and to intermediates formed during said process.

It is well known that certain mevalonate derivatives are active as hypercholesterolemic agents, which function by limiting cholesterol biosynthesis by inhibiting the enzyme HMG-CoA reductase. These mevalonate derivatives are the naturally occurring fungal metabolites lovastatin and compactin. Semi-synthetic and synthetic analogs thereof are also active.

The naturally occurring compounds lovastatin and compactin posess a 2-methylbutyrate side chain at the 8-position of the hexahydronaphthalene ring system. Analogs with a 2,2-dimethylbutyrate moiety at this position, such as simvastatin, appear to be more effective inhibitors of HMG-CoA reductase.

These compounds can be synthesized from the naturally occurring compounds. In principle, there are two possible routes for the introduction of an extra αmethyl group in the 8-acyl side chain which are:
1. direct alkylation of the 2-methylbutyrate side chain, and
2. removal of the 2-methylbutyrate side chain and introduction of a 2,2-dimethyl butyrate chain.

The main advantage of the direct alkylation route is the relatively high yields that can be obtained. However, there are several drawbacks. Direct methylation of unprotected lovastatin (U.S. Pat. No. 4,582,915) results in a rather impure simvastatin, containing a relatively high amount of unconverted lovastatin and many byproducts. Therefore, protection of the pyranone ring is required. Reduction of the byproducts was achieved by protecting the pyranone ring of lovastatin with t-butyl dimethyl silyl chloride prior to the alkylation (European patent EP299656). However, this is a very expensive protecting group. A less expensive protecting group is boronic acid as disclosed in international patent application WO 95/13283.

Nevertheless, this route still suffers from the fact that it is difficult to obtain a complete conversion of the 2-methylbutyrate side chain into the 2,2-dimethyl butyrate side chain. Therefore, an additional purification is necessary; for example, base hydrolysis of the remaining lovastatin to triol acid with NaOH or LiOH, in which part of the simvastatin is hydrolysed, followed by crystallization. Alternatively, selective enzymatic hydrolysis of lovastatin (U.S. Pat No. 5,223,415) may be utilized. However, these extra purification steps will reduce the yield, and make the process less efficient.

The second route, wherein the 2-methyl butyrate side chain is completely removed and another side chain is added, offers an intrinsically better quality product, as the separation of the hydrolyzed product and the esterified product is much easier to achieve compared to the unreacted starting material and the methylated product.

In U.S. Pat No. 4,293,496, the removal of the 2-methyl butyrate side chain is achieved by base hydrolysis of lovastatin with an alkali metal hydroxide, preferably LiOH. This reaction requires long processing time (50–72 hours while refluxing) or rather stringent conditions (120° C.–180° C.) if shorter processing times are used.

In U.S. Pat No. 4,444,784, the introduction of a new side chain to the hydrolyzed lovastatin is disclosed. It involves several separate steps: relactonization of the mevinic acid, protection of the hydroxy group in the pyranone ring by reaction with t-butyl dimethyl silyl chloride, esterification with 2,2-dimethyl butyric acid and deprotection of the hydroxy group of the pyranone ring. The main disadvantages of this process route are the low yields, and the use of an expensive protecting group, viz, t-butyl dimethyl silyl chloride.

A much less expensive protecting group is disclosed in U.S. Pat. 5,159,104. Instead of the t-butyl dimethyl silyl chloride protection of the OH-group in the pyranone ring, the OH-group was esterified with an acetic anhydride or an acylhalide. However, this process still suffers from a poor yield.

The present invention thus provides a new rather inexpensive, crystalline intermediate which can be used in both synthesis routes. In addition, a novel, quick and less expensive process for the quantitative removal of the 2-methyl butyryl side chain and addition of another side chain, is disclosed, including novel, crystalline intermediates for the preparation of semi-synthetic lovastatin and compactin intermediates. Further, a much higher yield for the removal of the side chain, about 95% was obtained compared to the yield of about 65% obtained in a comparable process as described by Askin et al. in J. Org. Chem. 1991, vol. 56, pages 4929–4932. Furthermore, by the application of the process of the present invention for the synthesis of semisynthetic statins, for example, simvastatin, the use of the carcinogen methyliodide is avoided, which is required in the direct methylation route.

The process of the present invention comprises a surprisingly selective removal of the 8'($R_3$')-side chain, for example, the 2-methyl butyryl side chain in lovastatin, thus forming a triol acid intermediate and another alcohol, by reduction with a reducing agent such as $LiAlH_4$ or a Grignard reagent, or to a triol acid intermediate and an amide by reaction with an amine. During this reaction, the starting material is quantitatively converted into the triol acid intermediate, which offers excellent possibilities for the introduction of various side chains.

SUMMARY OF THE INVENTION

Figure 1:
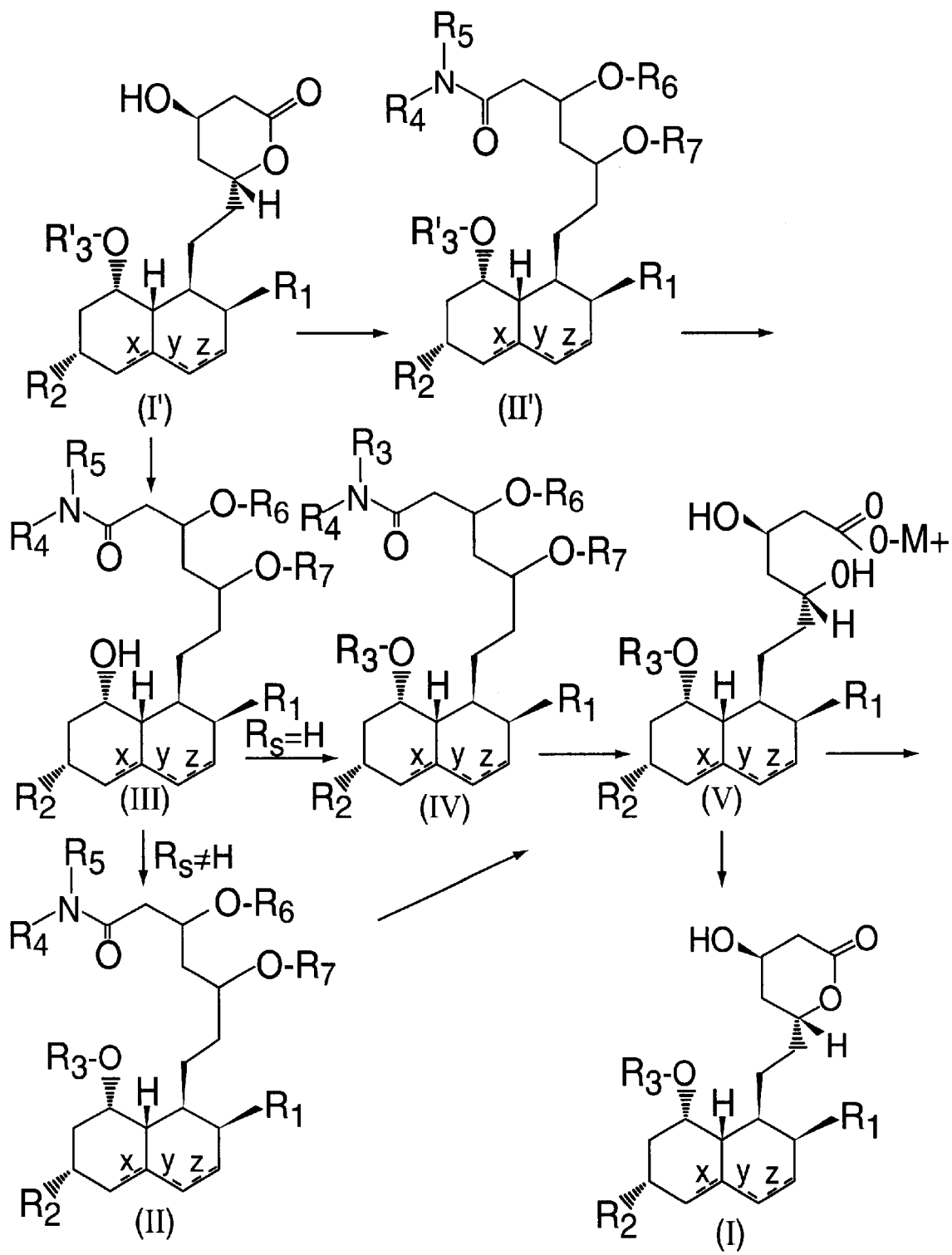
FIG. 1 is a schematic of the process for preparing semi-synthetic statins, depicted as formula I, from a statin, preferably a naturally occurring one, by removal of the 8'-side chain ($R_3$') including the novel intermediates of formula II and IV, depicted as II', III, IV and II. The figure shows only one of the possible stereoisomers and should not be regarded as limited thereto.

In one embodiment, the present invention provides a novel process for the production of semi-synthetic statins of formula I, in FIG. 1 from a statin of formula I'in FIG. 1, wherein R and $R_2$ are independently selected from the group consisting essentially of a hydrogen atom, a hydroxyl, $C_{1-10}$alkyl, $C_{6-14}$aryl and $C_{6-4}$aryl-$C_{1-3}$ alkyl, preferably methyl, and wherein $R_3$ and $R_3$'are independently selected from the group consisting of $R_9$—CO—and hydrogen, and wherein $R_9$ is selected from the group consisting of:

(1) $C_{1-15}$straight or branched alkyl,
(2) $C_{3-15}$cycloalkyl, (3) $C_{2-15}$alkenyl, straight or branched
(4) $C_{2-15}$alkynyl, straight or branched
(5) phenyl,
(6) phenyl$C_{1-6}$alkyl-, all optionally substituted with one or more of the substituents independently selected from the group consisting of halogen, $C_{1-6}$alkyl, $C_{1-6}$alkoxy, $C_{6-14}$aryl, for example, phenyl or aromatic heterocyclic.

Preferably, $R_3$ is 2,2-dimethylbutyryl and $R_3'$ is 2-methylbutyryl, and wherein the dotted lines at x, y and z represent possible double bonds, when any are present, being either x and z in combination or x, y or z alone or none, with the proviso that the double bonds of a compound as defined in formula I are the same as the double bonds of a compound as defined in formula I'. In this first embodiment, the process involves ring opening of the lactone by forming an amide bond by reaction with ammonia or with a primary amine, preferably n-butylamine or cyclohexylamine or a secondary amine, preferably piperidine or pyrrolidine, and subsequently optionally protecting the hydroxyl groups, for instance by formulation of a dioxane moiety at $R_6$ and $R_7$,

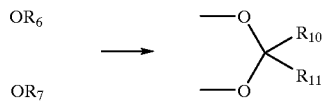

by reaction with a ketone, defined as $R_{10}$—CO—$R_{11}$, or an aldehyde defined as $R_{10}$—CO—H, or an acetal defined as

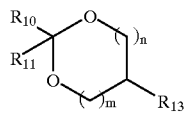

or $H(CH_2)_n CHR_{13}(CH_2)_m$—$OR_{10}CR_{11}O(CH_2)_m CHR_{13}'(CH_2)_n H$ wherein $R_{13}$ and $R_{13}'$are each independently selected from the group consisting of hydrogen, halogen, $C_{1-6}$alkyl-, $C_{1-6}$alkoxy, $C_{6-14}$aryl, for example, phenyl or aromatic heterocycle and m, n, m' and n' are each independently 0–10,
wherein $R_{10}$ and $R_{11}$, are each independently selected from the group consisting of:
(1) $C_{1-5}$alkyl, straight or branched,
(2) $C_{3-15}$cycloalkyl,
(3) $C_{2-15}$alkenyl, straight or branched
(4) $C_{2-15}$alkynyl, straight or branched
(5) phenyl,
(6) phenyl$C_{1-6}$alkyl-,
any of which is optionally substituted with one or more of the substituents independently selected from the group consisting of halogen, $C_{1-6}$alkyl, $C_{1-6}$alkoxy, $C_{6-14}$aryl, for example phenyl or an aromatic heterocyclic,
(7) hydrogen, with the proviso that $R_{10}$ is not hydrogen,
(8) $R_{10}$ and $R_{11}$ forming an optionally substituted 5, 6, 7 or 8 membered cyclic moiety, in which the substituents comprise halogen and a $C_{1-6}$alkyl in any combination, preferably $R_{10}$ and $R_{11}$ are methyl,
in the presence of a catalytic agent, preferably an acid such as para-toluene sulphonic acid (p-TsOH) or sulfuric acid, or by reaction with silylating agents, preferably t-butyl dimethyl silyl chloride,
or by formation of protective groups, such as for example:

(1) cyclic sulfate,

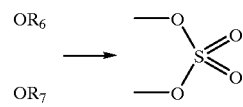

(2) cyclic phosphate,

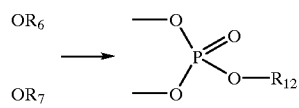

in which $R_{12}$ is selected from the group consisting of:
(1) $C_{1-15}$straight or branched alkyl,
(2) $C_{3-15}$cycloalkyl,
(3) phenyl
(4) phenyl-$C_{1-6}$alkyl
(5) hydrogen,
(6) primary amines, preferably n-butylamine or cyclohexylamine or secondary amines, preferably piperidine or pyrrolidine,
(3) borylidene

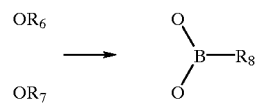

in which $R_8$ is phenyl optionally substituted by one to five substituents, halogen or $C_{1-6}$alkyl in any combination, preferably phenyl or para-fluoro-phenyl, followed by removal of the ester $R_3'$ moiety by reduction with suitable reducing agents, such as lithiumaluminumhydride, methylmagnesiumchloride or n-butyllithium, or by reaction with a primary amine $R_4NH_2$ wherein $R_4$ is selected from the group consisting of
(1) $C_{1-15}$ straight or branched alkyl,
(2) $C_{3-15}$cycloalkyl,
(3) $C_{2-15}$alkenyl, straight or branched,
(4) $C_{2-15}$alkynyl, straight or branched,
(5) phenyl,
(6) phenyl$C_{1-6}$alkyl-,
all optionally substituted with one or more of the substituents independently selected from the group consisting of halogen, $C_{1-6}$alkyl, $C_{1-6}$alkoxy, aryl, for example, phenyl or aromatic heterocycle,
(7) hydrogen,
followed by acylation with the acid chloride or the free acid of the corresponding $R_3$ group or the optionally symmetric anhydride, with the proviso that in case $R_6$ and $R_7$ are hydrogen, the corresponding hydroxyl groups are protected as described above before this acylation reaction is carried out, followed by the removal of the protective group and of the amide by hydrolysis, into a compound of formula V, depicted in figure I, wherein M forms any pharmaceutically acceptable salt, acid or ester thereof, optionally followed by lactonization by heating, and finally by crystallization.

The present invention also provides a number of novel intermediates of formulas II, II', and III in figure I, and of formula IV in figure I, wherein $R_1$ $R_2$, $R_3$, and $R_3'$ and the double bonds x, z and y are defined as above in formula I, and $R_4$ and $R_5$ are independently selected from the groups as defined for $R_4$ in $R_4NH_2$ above and $R_4$ and $R_5$ may form, together with the nitrogen to which they are attached, a 5, 6 or 7 membered heterocycle moiety such as a pyrrolidine, piperidine or a homopiperidine, and wherein $R_6$ and $R_7$ are independently selected from the group consisting of:

(1) a dioxane moiety, with $R_{10}$ and $R_{11}$, defined as above,
(2) a cyclic sulfate,
(3) a cyclic phosphate, with $R_{12}$ defined as above, and with the proviso that when $R_3$ is hydrogen, $R_6$ and $R_7$ may also form a borylidene group, wherein $R_8$ is defined as above and $R_6$ and $R_7$ may be both hydrogen.

The processes disclosed for the preparation of said intermediates above form a substantial part of the invention.

In another embodiment, the present invention provides for the preparation of a compound of formula I, as described above, with the proviso that $R_3$ comprises an alkyl group on the α-position, from a compound of formula I', as described above, with the proviso that $R_3'$ comprises a hydrogen on the α-position, followed by ring opening of the lactone by forming an amide bond by reaction with ammonia or with a primary amine, preferably n-butylamine or cyclohexylamine or a secondary amine, preferably piperidine or pyrrolidine, and subsequently, optionally protecting the hydroxyl groups, for instance by formation of a dioxane moiety at $R_6$ and $R_7$, with $R_{10}$ and $R_{11}$ defined as above, followed by direct α-alkylation of the $R_3'$ moiety in formula II' in Figure I, thus forming a compound of formula II, defined as above, with the proviso that $R_3$ comprises an alkyl group on the α-position, exemplified in figure II, by reaction with an alkyl halide, for instance methyl iodide (MeI).

The present invention provides for the use of the processes as described above for preparing a compound of formula I, as described above, from a compound of formula I', as described above, containing up to about 30% of impurities, for example, oxidized compounds or di-or tetrahydro statins. Preferably, simvastatin is produced in this way, starting from lovastatin contaminated with dihydrolovastatin and optionally oxidized compounds.

DETAILED DESCRIPTION OF THE INVENTION

The process of the invention comprises the following steps:
(1) Conversion of a compound of formula I', defined as above into a compound of formula II' defined as above, by:
  (a) ring opening of the lactone by formation of an amide bond with an excess of amine, optionally mixed with an inert organic solvent for example, toluene, cyclohexane, tetrahydrofuran, acetonitrile; preferably, the amine has a boiling point higher than 60° C., at a temperature above about room temperature, preferably higher than 60° C., where after complete conversion, the excess of amine is removed; for example, by evaporation, or by washing with dilute acid,
  (b) optionally followed by protecting the hydroxy groups resulting from the ring opening of the lactone by reaction of the resultant amide with a ketone or aldehyde or acetal, optionally mixed with an inert organic solvent, for example toluene, cyclohexane, tetrahydrofuran, acetonitrile or ethylacetate, between 5° C. and 50° C., preferably around room temperature, in the presence of a catalytic agent, for example p-toluene sulphonic acid (p-TsOH) or sulfuric acid, or by reaction of the resultant amide with sulfonyl chloride in dichloromethane at a temperature between –20° C. and 20° C., preferably between –5° C. and 5° C., followed by oxidation to form the sulfate, for example with sodium periodate in a suitable solvent, for example a mixture of water and acetonitrile in the presence of a catalyst, for example ruthenium chloride,
or by reaction of the resultant amide with phosphonyl chloride in an inert organic solvent, for example toluene at a temperature between 5° C. and 50° C., preferably between 15° C. and 25° C., followed by reaction with an alcohol, or an amine or water;
or the formation of a borylidene moiety as described in International patent application WO 95/13283 mentioned above,
or the reaction with t-butyl dimethylsilyl chloride as described in US Pat. No. 4,444,784 mentioned above, (2) Conversion of the compound of formula II' formed in step 1 to a compound of formula III as defined above, by removal of the $R_3'$ moiety with a suitable reagent, for example:
  (a) by reduction with lithium aluminum hydride, aluminum hydride or diisobutyl aluminum hydride in an inert solvent, for example, toluene or tetrahydrofuran (THF) at a temperature between 0° C. and 30° C., preferably between 5 ° C. and 10° C., whereafter, the reaction mixture is neutralized with, for example, water or potassium hydroxide or sodium hydroxide or ethylacetate to neutralize the excess of lithium aluminum hydride,
  (b) by reduction with an organo-metallic compound such as a Grignard reagent in an inert solvent, for example, THF at a temperature between –10° C. and 20° C., preferably between –5° C. and 10° C., or with an alkyl lithium compound, for example, n-butyllithium, in an inert solvent, for example, THF at a temperature between –70° C. and –20° C.,
  (c) by reaction with a primary amine or ammonia, preferably at a molar ratio equal to or greater than 1:1 with respect to the compound of formula II', optionally in the presence of water or an organic solvent, at a temperature between about 100° C. and 250° C., preferably between about 130° C. and 200° C., optionally at superatmospheric pressure, dependent on the boiling points of the reactants and solvents applied.

(3) Conversion of the compound of formula II as defined above, with the proviso that $R_3$ is hydrogen (depicted as formula III in Figure I) formed in step 2 to a compound of formula IV where $R_5$ is hydrogen, or a compound of formula II where $R_5$ is not hydrogen, defined as above, by acylation with
  (a) the corresponding acid chloride in the presence of a base, such as triethylamine as a scavenger for HCl or with
  (b) the corresponding free acid optionally in the presence of a carbodiimide such as 1,3 dicyclohexylcarbodiimide or
  (c) the corresponding optionally symmetric anhydride, in an organic solvent in the presence of a catalyst, for example 4-dimethylaminopyridine (DMAP), at a temperature between 20° C. and 1 10° C., preferably between 80° C. and 110° C.

(4) Conversion of a compound of formula II, formed in step 3, to a compound of formula V defined as above, by:
  (a) removal of the protecting groups at $R_6$ and $R_7$, for example, by hydrolysis in a mixture of water and an organic solvent, such as THF in the presence of a catalyst, for example, hydrogen chloride or sulphuric acid or p-TsOH at a temperature between 20° C. and 100° C., preferably between 30° C. and 70° C., (b) followed by the removal of the amide by hydrolysis thereof, as for example, in a mixture of a solution of sodium hydroxide or potassium hydroxide in water and an organic solvent, as for example, methanol, ethanol, toluene or tetrahydrofuran, (c) optionally, followed by reacting with an agent to form a compound of formula V, preferably with a base corresponding to a pharmaceutically acceptable salt, in an organic solvent, for example, methanol, toluene or ethylacetate to form the corresponding salt, for example the ammonium salt.

(5) Conversion of the compound of formula V, formed in step 4, into a compound of formula I, defined as above, by lactonization of the compound V in an inert solvent, for example, toluene, ethyl acetate or cyclohexane at a temperature between 60° C. and 110° C., preferably between 80° C. and 100° C. Finally, isolating the compound of formula I by a crystallization method known in the art.

It should be noted that using an amine for the removal of the $R_3$'-moiety as described in reaction step 2c of the process of the invention offers the possibility to combine the amide formation of reaction step 1a with 2c, whereby a compound of formula I, depicted as I' in FIG. 1 is directly converted into a compound of formula III, where R6 and $R_7$ are each hydrogen.

It should further be noted that the process and compound provided by the present invention are not limited to the stereoisomers depicted in FIG. 1.

By an aryl group is meant an aromatic hydrocarbon group, for example, phenyl, naphthyl, anthryl or an aromatic heterocycle comprising for example a nitrogen, a sulfur or oxygen atom.

By a corresponding amine is meant an amine, defined as $R_4R_5NH$, with $R_4$ and $R_5$ defined as above, reacting with a compound of formula I', defined as above, resulting in a compound of formula II', defined as above, wherein $R_6$ and $R_7$ are hydrogen and an $R_4R_5NCO$ amide bond is formed, wherein $R_4$ and $R_5$ are the same as in the amine used.

By a corresponding acylation agent is meant a compound of formula $R_3P$, where P is OH or Cl or an anhydride $R_3O—CO—O—R_{14}$, where $R_3$ is defined as above with the proviso that $R_3$ is not hydrogen and $R_{14}$ is defined as $R_3$, optionally $R_4$ is the same as $R_3$ resulting in a symmetric anhydride, which upon reaction with a compound of formula III, defined as above, results in a compound of formula IV, defined as above, or a compound of formula II, defined as above, wherein $R_3$ is the same as in the acylation agent used.

In all processes of the present invention, the possible double bonds x, y and z of the starting compounds are the same as those in the end products. Furthermore, unless otherwise indicated, all other R groups remain the same for the end product as for the starting material.

Surprisingly, it was found that in the process of preparing pure simvastatin from lovastatin, impure lovastatin may be used, which may contain up to about 30% of impurities, such as dihydrolovastatin or oxidized lovastatin.

EXAMPLES

Experimental

The HPLC-analyses were carried out according to A. Houck et al., Talanta, Vol. 40 (4), 491–494 (1993):

"Liquid Chromatographic determination of the known low level impurities in lovastatin bulk drug: an application of high-low chromatography."

HPLC
  Alliance Waters pump/injector
  M966 diode array Waters
  Millennium data system Waters
  column: Prodigy 5 C8 250×4.6 mm (phenomenex)
Conditions:
  injection volume: 10 µl
  gradient flow profile (lineair)
  A=acetonitrile
  B=0.1% $H_3PO4$

| TIME min | FLOW ml/min | % A | % B |
|---|---|---|---|
| 0 | 1.5 | 60 | 40 |
| 1 | 1.5 | 60 | 40 |
| 5 | 1.5 | 80 | 20 |
| 8 | 1.5 | 90 | 10 |
| 16 | 1.5 | 90 | 10 |
| 20 | 1.5 | 60 | 40 | column temperature 30° C.

Detection at 200 nm and 237 nm.

The samples were mixed in acetonitrile with a concentration of 1.5 mg/ml.

Retention times:

| dihydro simvastatin | 8.10 min (200 nm) |
|---|---|
| simvastatin acid | 5.77 min (237 nm) |
| lovastatin | 6.34 |
| simvastatin | 7.11 |
| dehydro simvastatin | 8.90 |
| dimer simvastatin | 15.36 |

Example 1

Formation of Lovastatin Piperidinamide

A mixture of 1 g (2.5 mmol) of lovastatin, 10 ml (0.1 mol) of piperidine, 100 mg (0.82) mmol) of N,N-dimethylaminopyridine and 30 ml of toluene was refluxed for 36 hours. The mixture was cooled to room temperature and washed with 2×30 ml of 2 N HCl and 2×20 ml of water. The organic layer was dried with sodium sulfate, filtered and evaporated. The residue was stirred with hexane and the resulting precipitate was filtered to give 0.87 g of lovastatin piperidinamide as a white solid.

Example 2

Reaction of Lovastatin Butilamide with Thionyichloride 0.76 g (715 mmol) of triethylamine was added to a solution of 1.2 g (2.5 mmol) of lovastatin butylamide in 20 ml of toluene. 0.45 g (3.7 mmol) of thionylchloride was added dropwise. After 1 hour at room temperature, the reaction mixture was washed with water, dried (sodium sulphate), filtered and evaporated to give a brown oil.

Example 3

Reaction of Lovastatin Butylamide with Phosphorylchloride 0.76 g (7.5 mmol) of triethylamine was added to a solution of 1.2 g (2.5 mmol) of lovastatin butylamide in 20 ml toluene. Next, 0.58 g (3.8 mmol) of phosphoryl chloride was added dropwise. After 1 hr at room temperature, the reaction mixture was filtered, dried (sodium sulphate), filtered and evaporated to give a brown oil.

Example 4

Process for Preparing Simvastatin by Direct Methylation

A. Formation of the Acetonide of Lovastatin Butylamide, Exemplified as Formula II' in FIG. II A mixture of 40 g (98 mmol) of lovastatin and 60 ml of n-butylamine was refluxed for 1 hour, evaporated and coevaporated twice with 100 ml of toluene. The resulting crude amide was dissolved in 500 ml of acetone and 3 g of p-TsOH was added. The clear solution was stirred at room temperature (RT) for two hours at which time a solid was formed. The mixture was cooled to −10° C. for three hours and the solid was collected and dried to afford 45 g (88%) of the amide/acetonide as a white solid. From the mother-liquor another 5 g was obtained, by partial evaporation of the solvent.

B. Alkylation of Amide/Acetonide Intermediate Formed in Step A

The amide/acetonide (19.5 g, 37.6 mmol) in 280 ml THF/cyclohexane (4/1) was cooled to −40° C. and 113 ml 1M lithium-pyrrolide (prepared from pyrrolidine and n-butyl lithium at −15° C.) was added maintaining the temperature at <−30° C. The solution was stirred at −35° C. for two hours and 5 ml MeI was added in one portion. The solution was stirred at −30° C. for one hour and the temperature was allowed to rise to −10° C. 300 ml of 1N HCl was added and the resulting mixture was refluxed for one hour. Ethyl acetate (300 ml) was added and the organic layer was washed with 100 ml of 3N HCl and evaporated.

300 ml of methanol and 125 ml of 2N NaOH were added to the residue. The mixture was refluxed for 12 hours and most of the methanol was evaporated. 120 ml of water and 300 ml of ethyl acetate were added and the pH was adjusted to 5 with 3N HCl. To the organic layer were added 60 ml of methanol and 25 ml of NH$_4$OH/methanol (1/3). The resulting mixture was stirred for one hour at room temperature and then cooled to 10° C. The solid was collected and dried. The yield was 13.5 g (80%) of simvastatin ammonium salt.

Example 5

Process for Preparation of Simvastatin from Lovastatin by Reduction of the $R_3$ Ester Moiety A. Formation of the Acetonide of Lovastatin Butylamide A mixture of lovastatin (40.5 g, 100 mmol) and 75 ml of n-butylamine was heated at reflux for 1 hour. The excess of amine was evaporated and coevaporated with 100 ml of toluene. To the crude amide was added 400 ml of acetone and 5 g of p-TsOH. The mixture was stirred at room temperature for 1 hour and then cooled in ice/water for 2 hours. The resulting solid was collected by filtration and dried. From the mother-liquor a second batch was obtained. Total yield 49 g (94–95%).

B1. Reduction of the Intermediate Formed in Step A with Lithium Aluminum Hydride The compound as formed in step A (45 g, 87 mmol) dissolved in 200 ml of THF and added dropwise to a suspension of 7 g (2.1 equivalents) of lithium aluminum hydride (LiAlH$_4$) in 100 ml of THF at 10–15° C. for about 20 minutes. The mixture was stirred for 30 minutes. The reaction mixture was treated with a solution of 20% KOH (exothermic). The resulting salts were removed by filtration and washed with 200 ml of THF. The combined filtrates were evaporated to afford 35.5 g of a syrup.

B2. Reduction of the Intermediate Formed in Step A with Methyl Magnesium Chloride (Grignard)

A solution of 2 g (3.9 mmol) of the compound as formed in step A, in 20 ml of THF was cooled to 0° C. A solution of 12 ml of 3M methyl magnesium chloride was added dropwise in 20 minutes. After 18 hours at room temperature the lovastatin n-butylamide acetonide was converted completely.

B3. Reduction of the Intermediate Formed in Step A with N-Butyl Lithium

A solution of the compound as formed in step A (a g, 1.9 mmol) in 25 ml THF was cooled to −50° C. A solution of 2.5 M n-butyllithium (2.74 ml) was added dropwise over a period of 10 minutes. After 18 hours stirring at room temperature, the alcohol intermediate was formed.

C. Acylation of the Intermediate Formed in Step B and Conversion to Ammonium Salt of Simvastatin 3 g of 4-dimethylaminopyridine in 300 ml of pyridine was added to a solution of 25 g (57 mmol) of the intermediate formed in step B and the mixture was heated to 50–55° C., preferably 50° C. 2,2-Dimethylbutyric acid chloride (50 ml) was added in one portion and the resulting mixture was stirred for 40 hours (HPLC-analysis showed complete conversion). To the reaction mixture, 400 of ml water and 400 ml of ethylacetate (EtOAc) was added. The organic layer was subsequently washed twice with 10% NaHCO$_3$ (400 ml), with water (400 ml) and with a solution of 10% HCl (400 ml). The organic layer was evaporated and dissolved in 200 ml of THF, 200 ml water was added, followed by 10 g of p-TsOH. The mixture was refluxed for 2 hours. EtOAc (400 ml) was added, followed by 300 ml water. The organic layer was washed twice with 10% NaHCO$_3$ (400 ml) and evaporated. The residue was dissolved in 300 ml of MeOH and 170 ml of 2N NaOH was added. The resulting mixture was refluxed for 3 hours and cooled to room temperature. Most of the MeOH was evaporated and 120 ml of water was added. The pH was adjusted to pH=7 with 2N HCl and 300 ml of EtOAc was added. The pH was further adjusted to pH=4 and the layers were separated. To the organic layer was added 100 ml of EtOH, followed by 40 ml of NH4OH/MeOH (1/3). The mixture was stirred at −10° C. for 2 hours and the solid collected and washed with EtOAc and EtOH (cold). Yield 16 g (62%), HPLC-analysis gave 98.9% of the ammonium salt of simvastatin.

D. Conversion of the Simvastatin Ammonium Salt to Simvastatin

A suspension of 9 g of the ammonium salt of simvastatin as formed in step C was heated in 250 ml of toluene at 100° C. for 6 hours. The mixture was refluxed for an additional 30 minutes, filtered and evaporated. To the residue, 100 ml of cyclohexane was added and the solution was evaporated again. The crude simvastatin was recrystallised from about 150 ml of cyclohexane to afford simvastatin as a white solid. Yield 85%, HPLC-analysis gave 98.4% of simvastatin.

Example 6

Process for the Preparation of Simvastatin from Lovastatin by Reduction of the $R_3$ Ester Moiety A. Preparation of the Acetonide of Lavastatin Butyl Amide A mixture of 950 g of lovastatin (2.4 mol), 8 l of toluene and 500 ml of n-butylamine (5 mol) is heated up to 85° C. under nitrogen. The solution is kept at 85° C.–95° C. during 2 hours, and is subsequently cooled to room temperature. Then, 5 l of 4 N sulfuric acid is added and the mixture is stirred during 5 minutes. The lower layer is removed, and 1.5 l (12 mol) of 2,2-dimethoxy propane are added to the upper layer. The solution is stirred during 30 minutes at room temperature, and thereafter the mixture is concentrated to 5.4 kg by evaporation at 55–60° C. under vacuum.

B. Reduction of the Intermediate Formed in Step A with Lithium Aluminum Hydride 5.8 l (5.5 kg, corresponding to 2.4 mol of the intermediate obtained in step A) of the concentrate obtained in step A is mixed with 2 l of toluene. The mixture is cooled to 0° C. under a nitrogen atmosphere. 6 L of a 1 N solution of Lithium aluminum hydride in toluene (6 mol $LiAlH_4$) is added over a period of 75 minutes, during which the temperature is kept below 8° C. The resulting mixture is stirred for 3 hours at 5–10° C., then 5.3 l of water is added over a period of 100 minutes, keeping the temperature below 10–15 ° C.

Subsequently, 5 l of 4N sulfuric acid is added to the suspension and the mixture is stirred during 15 minutes. Thereafter, the layers are allowed to settle. The milky lower layer is removed, and the upper layer is washed with 4.5 l of water and with 6 l of an aqueous 1 N sodium hydroxide solution. 6 L of the upper layer are removed by evaporation at 50–60° C. under vacuum (150–300 mm Hg).

C. Acylation of the Intermediate Obtained in Step B with 2,2-dimethyl Butyryl Chloride To the solution of the alcohol intermediate in toluene obtained in step B, containing 2.4 mol of intermediate, 250 ml of toluene containing 35 g (0.29 mol) of 4-(N,N-dimethyl amino) pyridine, 1.6 l of triethylamine (11.4 mol) and 1.5 kg (11 mol) of 2,2-dimethyl butyryl chloride are added. The resulting solution is heated to 105–110° C., and stirred at this temperature during 10 hours under nitrogen.

Thereafter, the resulting suspension is cooled to room temperature, and 3 l of 4 N sulfuric acid is added. The mixture is stirred for 5 minutes, and then the layers are allowed to separate. Subsequently, the lower layer is removed, and the upper layer is washed with 2 l of 4 N sulfuric acid.

D. Preparation of simvastatin ammonium salt

The reaction mixture obtained in Step C (about 11 l) is mixed with 4.5 l of 4 N sulfuric acid. The mixture is subsequently heated at 70–75 ° C. during 3 hours, while nitrogen is led through the mixture. Then the mixture is allowed to cool to room temperature, and the lower layer is removed. The upper layer is cooled to 5° C. and washed with 2.5 l of 2 N sodium hydroxide. After removal of the lower layer, 6 l of 2 N sulfuric acid is added and stirred during 3 hours at room temperature, and then at 45–55° C. during 3 hours. The suspension is cooled to 5–10° C., whereafter 2.75 l of 4N sulfuric acid is added while the temperature is kept below 10° C. Then, the lower layer is removed, and 1 l of a concentrated $NH_4OH$ solution is added. Subsequently, the mixture is concentrated at 50–60° C. under vacuum in order to remove toluene and water. 3 l of ethyl acetate is added to the residue, and the mixture is stirred at 50° C. during 30 minutes to obtain a homogeneous suspension. The suspension is cooled to room temperature and filtered under vacuum. The filter cake is subsequently washed with 1 l of ethyl acetate and subsequently it is suspended in 4 l of ethyl acetate, heated at 50° C. for 90 minutes, the warm suspension is filtered and the filter cake is washed in ethyl acetate, yielding 891 g of crystals of simvastatin ammonium salt.

E. Preparation of Simvastatin 570 g of the ammonium salt crystals as obtained in step D are suspended in 13 l of toluene. Subsequently, 2 l of water is added, and the pH is adjusted to 3 by addition of 4 N sulfuric acid. The mixture is stirred during 30 minutes, whereafter the lower layer is removed. The upper layer is subsequently washed with 2 l of water, and concentrated by evaporation of 4 l of toluene at 50–60° C. under vacuum. The remaining solution is heated at 85–92° C. under nitrogen during 2.5 hours. Then, the solution is cooled to 15 ° C., 3 l of water is added and the pH is adjusted to pH 8–8.5 by addition of a solution of 1 N NaOH. The lower layer is removed and 3 l of water is added to the upper layer followed by adjustment of the pH to 6 by adding 6N sulfuric acid.

The lower layer is removed, and the upper layer is concentrated to 1 l by evaporation at 50–60° C. under vacuum. Subsequently, 350 ml of n-hexane is added over a period of 1 hour at 50–60° C. Subsequently, the mixture is stirred at 50–60° C. during 30 minutes and then slowly cooled to 15° C. over a period of 2 hours. The crystals are filtered and washed with 350 ml of a mixture of n-hexane/toluene (5/1), yielding 440 g of simvastatin.

Example 7

Process for the Preparation of Simvastatin Ammonium Salt by Reduction of the $R_3$ Ester Moiety of Lovastatin A. Formation of Lovastatin Cyclohexanamide A mixture of 5 g (0.012 mol) of lovastatin, 6 ml (0.052 mol) of cyclohexylamine and 50 ml of toluene was refluxed for 6 hours. The reaction mixture was cooled to room temperature and 20 ml of ethylacetate was added. The mixture was washed with 2N HCl (2×30 ml) and water (2×20 ml). The organic layer was dried with sodium sulfate, filtered and evaporated to a volume of 15 ml. 50 ml of hexane was added and the precipitate was filtered to give 5.5 g of lovastatin cyclohexanamide as a white powder.

B. Formation of Lovastatin Cyclohexanamide Acetonide

To a solution of 5 g (10 mmol) of lovastatin cyclohexanamide in 25 ml of acetone was added 300 mg (1.6 mmol) of p-TsOH. After 18 hours stirring at room temperature the solution was poured into a mixture of 50 ml ethylacetate and 50 ml, 10% sodium bicarbonate solution. The ethylacetate layer was separated, washed with 30 ml, 10% sodium bicarbonate solution, dried with sodium sulfate, filtered and evaporated. The residue was dissolved in toluene which was subsequently evaporated to give 4.9 g of the acetonide of lovastatin cyclohexanamide.

C. Formation of Simvastatin Ammonium Salt

A suspension of 836 mg (22 mmol) of lithium aluminum hydride in 15 ml of THF was cooled to 0° C. and a solution of 4.93 g (9.1 mmol) of the compound formed in step B, in 20 ml of THF was added dropwise over a period of 15 minutes. After 18 hours at room temperature the reaction mixture was cooled to 0° C. and 1 ml of water and of a 10% potassium hydroxide solution were added subsequently. The mixture was filtered over Celite and the THF was evaporated to give 4.3 g (9 mmol) of the corresponding alcohol intermediate.

D. Formation of Simvastatin Ammonium Salt

A mixture of 4.3 g (9 mmol) of the alcohol intermediate, 40 m of pyridine, 200 mg N,N-dimethylaminopyridine and 7.2 g, (5 mmol) of 2,2-dimethylbutyric acid chloride was stirred for 7 hours at 65° C. The mixture was cooled, 100 ml of toluene was added and the mixture was washed with 2×50 ml of a 10% sodium bicarbonate solution and 30 ml of brine. The toluene layer was dried with sodium sulfate, filtered and evaporated. The residue was dissolved in 100 ml of toluene which was subsequently evaporated.

The residue was dissolved in 20 ml of THF and 20 ml of water. Next, 1 g of p-TsOH was added and the solution was refluxed for 5 hours. The solution was poured into a mixture of 70 ml of toluene and 50 ml of 10% sodium bicarbonate solution. The organic layer was separated and washed with 30 ml of 10% sodium bicarbonate solution. The organic layer was dried, filtered and evaporated to give 4.8 g residue. The residue was dissolved in 70 ml of methanol and 40 ml of 2M NaOH. The reaction mixture was refluxed for 72 hours. The methanol was evaporated and the water layer was cooled to 0° C. The water layer was acidified to pH=5 with a 2N HCl solution. Next, 75 ml of ethylacetate was added and the organic layer was separated. To the ethylacetate was added 5 ml 25% of ammonia solution. The precipitate was filtered to give 1.1 g of the ammonium salt of simvastatin, with an overall yield of 27% from the acetonide of lovastatin cyclohexanamide.

Example 8

Preparation of Diacylated Simvastatin Butylamide

A. Silylation of Lovastatin Butylamide

T-butyl dimethylsilyl lovastatin butylamide was prepared by literature procedure (Askin D.; Verhoeven, T. R.; Liu, T, M. -H.; Shinkai, I. *J. Org. Chem.*, 1991, 56, 4929) and obtained with a yield of 68% (crude material), HPLC $R_f$: 12.87.

B. Reduction of t-butyl Dimethylsilyl Lovastatin Butylamide

A solution of t-butyl dimethylsilyl lovastatin butylamide (1.65 g, 2.34 mmol) in THF (30 ml) was added to a 1M solution of LiAlH$_4$.2THF in toluene (6 ml, 2.5 eq,) at 0° C. The reaction mixture was stirred for 2 h, after which moist sodium sulfate (Na$_2$SO$_4$.nH$_2$O) was added until gas evolution ceased. Attempts to filter the slurry over a glass funnel (P2) with Celite layer failed. The reaction mixture was poured in dilute HCl (<1N). The water layer was extracted with diethylether. The organic layer was washed with brine, dried (Na$_2$SO$_4$) and evaporated.

Yield: 1.07 g (89%).

HPLC: $R_f$:9.$^{27}$.

C. Acylation of t-butyl Silyl Protected Lovastatin Butylamide Alcohol

To a solution of the alcohol intermediate obtained in step 8B (360 mg, 0.58 mmol) and triethylamine (0.32 ml) in toluene (10 ml), 2,2-dimethylbutyryl chloride was added (0.31 g, 4 eq.). The reaction mixture was heated to reflux for 10h (standard procedure). HPLC analysis showed a mixture of compounds among which included the desired diacylated product (R: 15, 81). Removal of the protecting groups according to the method described in Askin D., Verhoeven, T. R.; Liu, T, M. -H.; Shinkai, I. *J Org. Chem.*, 1991, 56, 4929) and obtained with a yield of 68% (crude material), HPLC $R_f$:2.87.

Example 9

Preparation of the Diacetylbenzylidene Derivative of Lovastatin

A. Formation of the Benzylidene Derivative of Lovastatin Butylamide

The lovastatin butylamide (4.77 g, 10 mmol) was dissolved in toluene (50 ml). Thereafter, benzaldehyde (10.6 g, 10 eq) and p-TsOH (500 mg) were added and stirred during 16 hours at room temperature. A saturated aqueous solution of NaHCO$_3$ was added and the layers were separated. The toluene layer was washed with saturated NaHCO$_3$ (aq), saturated NaCl (aq), dried (Na$_2$SO$_4$) and evaporated. The residue was purified further by applying column chromatography (SiO$_2$)/n-Hexane/ethylacetate, which yielded 2.6 g (46%) of the endproduct.

B. Reduction of the Benzylidene Derivative

The benzylidene derivative (2.6 g, 4.6 mmol) was dissolved in toluene (50 ml) and the solution was cooled to 0° C. Then, a solution of 1M LaAlH.2THF (11.5 ml) in toluene was added dropwise while the temperature was kept under 10° C. Then, the solution was stirred for 2 hours at 0–5° C. Thereafter, 30% NaOH (aq, 1.8 ml) was added and the mixture was stirred for 16 hours at room temperature. The mixture was filtered over Celite, washed with toluene (50 ml) and concentrated to about 50 ml.

C. Formation of the Benzylidene Derivative of Simvastatin

Triethylamine (1.9 g, 4.1 eq), dimethylbutyric acid (2.5 g, 4 eq) and dimethylaminopyridine (50 mg) were added to the reaction mixture formed in step 9B and refluxed for 16 hours. The mixture was then poured into water/ethylacetate and separated.

The organic layer was subsequently washed with water, followed by saturated sodium chloride, then dried with sodium sulfate and evaporated, yielding 3.3 g of crude product.

Further conversion of the product to simvastatin is carried out according to the procedure described in Example 5C and 5D, second part.

Example 10

Lovastatin Reduction of the Acetonide of Lovastatin Pyrrolidin Amide

40 Mg (1.1mmol) of lithium aluminum hydride was added at 0° C. to a solution of 1 g (1.94 mmol) of the acetonide of lovastatin pyrolidine butylamide (prepared analogous to the method described in example 3 by reaction of lovastatin and pyrrolidine) in 20 ml THF. After 18 hours at room temperature, the conversion was 50%.

Example 11

Reduction of Lovastatin Butylamide

To a suspension of LiAlH$_4$ (400 mg 10.5 mmol) in THF (50 ml) was added a solution of lovastatin butylamide (2.25 g, 5 mmol) in THF (25 ml) at 0° C. The mixture was stirred for 16 h at ambient temperature. Moist sodium sulfate (Na$_2$SO$_4$n2H$_2$O, Glauber salt analogue) was added until gas evolution cased after which dry (Na$_2$SO$_4$ was added. The slurry was filtered over a glass filter and the filtrate was evaporated under reduced pressure to dryness to give a thick brown oil (1.03 g, 53%) HPLC of the crude material; R$_1$; 2.93 (and 5.79, starting material).

Example 12

Selective Acylation Reaction on the Nitrogen of the Lovastatin Butylamide Acetonide Alcohol, Hereafter the OH Group can be Acylated To a solution of lovastatin butylamide acetonide alcohol (2.1 g, 5 mmol) and triethylamine (0.8 ml, 5.5 mmol) in toluene (50 ml) was added 1.1 eq. benzoyl chloride (0.64 ml, 5.5 mmol) at 0° C. The reaction mixture was stirred for 16 h at room temperature. An HPLC sample displayed major peaks at R$_f$ 6.16 (starting material) and 9.13. After 21 h a peak at 9.67 was coming up. NMR analysis showed a small NH peak and 3 other peaks in the region 6.5-5 ppm, indicating that the amide is acylated.

Example 13

Reaction of Lovastatin with Ammonia

A suspension of 0.25 g (0.6 mmol) lovastatin in 15 ml of methanol was cooled to 5° C. on an ice/water bath. The methanol was saturated with ammonia (gas) and the mixture was heated for 40 hours at 130° C. in a sealed tube. The reaction mixture contained 43% of the corresponding deacylated product according to HPLC-analysis.

Example 14

Reaction of Lovastatin with n-butylamine

A solution of 0.5 g (1.2 mmol) of lovastatin in 15 ml of n-butylamine was heated for 40 hours at 150° C. in a sealed vessel. The reaction mixture contained 12.3% of the corresponding deacylated product according to HPLC analysis. The structure of the deacylated butylamide was confirmed by forming the corresponding acetonide by reaction with pTsOH and acetone and comparing the acetonide with another sample of acetonide made by the process described in the second part of example 5A.

Example 15

Reaction of Lovastatin with n-heptylamine

A solution of 0.25 g (1.2 mmol) of lovastatin in 10 ml of heptylamine was refluxed for 70 hours. The resulting reaction mixture contained 17% of the corresponding deacylated product according to HPLC analysis.

Example 16

All three deacylated compounds from Examples 13, 14 and 15 were converted into the corresponding acetonide (i.e. by ring closure) by addition of 400 ml of acetone and 5 g of p-TsOH. The mixture was stirred for 1 hour (at room temperature) and then cooled in ice water for 2 hours. The resulting solid was collected by suction and dried.

Example 17

The three acetonide compounds resulting from Example 16 were then each individually converted to simvastatin using the acylation and ammonium salt conversion reactions as described in steps C and D of Example 5.

What is claimed is:

1. A compound of formula II,

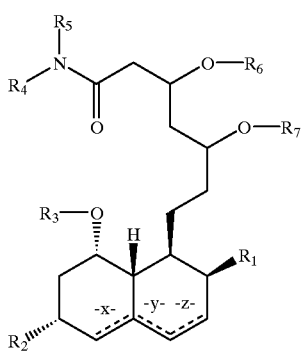

(II)

wherein $R_1$, and $R_2$, are independently selected from the group consisting of a hydrogen atom, a hydroxyl, $C_{1-10}$alkyl and $C_{6-14}$aryl and $C_{6-14}$aryl$C_{1-3}$alkyl, and wherein $R_3$ is $R_9$-C=O or hydrogen, and wherein each of $R_9$, $R_4$ and $R_5$ are independently selected from the group consisting of:

(1) $C_{1-15}$alkyl, straight or branched,
(2) $C_{3-15}$cycloalkyl,
(3) $C_{2-15}$alkenyl, straight or branched,
(4) $C_{2-15}$alkynyl, straight or branched,
(5) phenyl and
(6) phenyl$C_{1-6}$alkyland $R_9$ may also be each of the definitions mentioned under (1) to (6) substituted with one or more of the substituents independently selected from the group consisting of halogen, C1-6alkyl, $C_{1-6}$alkoxy and $C_{6-14}$aryl, and $R_4$ and $R_5$ may also be hydrogen or form with the nitrogen to which they are attached, a 5, 6 or 7 membered heterocycle moiety, and wherein $R_6$ and $R_7$ are also independently selected from the group consisting of:

(1) a dioxane moiety,

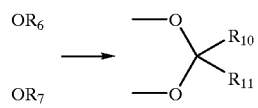

wherein $R_{10}$ and $R_{11}$ are independently selected from the group consisting of:
(1) $C_{1-15}$ alkyl, straight or branched,
(2) $C_{3-15}$cycloalkyl,
(3) $C_{2-15}$alkenyl, straight or branched,
(4) $C_{2-15}$alkynyl, straight or branched,
(5) phenyl, and
(6) phenyl$C_{1-6}$alkyl-,
all optionally substituted with one or more of the substituents independently selected from the group consisting of halogen $C_{1-6}$alkyl, $C_{1-6}$alkoxy or $C_{6-14}$aryl,
(7) hydrogen, with the proviso that $R_{10}$ is not hydrogen,
(8) $R_{10}$ and $R_{11}$ form an optionally substituted 5, 6, 7 or 8 membered cyclic moiety, in which one or more of the substituents; is selected from the group consisting of halogen and a lower alkyl in any combination, (2) a cyclic sulfate,

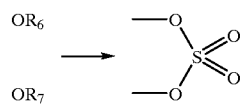

(3) or a cyclic phosphate,
in which $R_{12}$ is selected from the group consisting of:

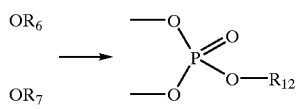

(1) $C_{1-15}$ alkyl, straight or branched,
(2) $C_{3-15}$cycloalkyl,
(3) phenyl,
(4) phenyl$C_{1-6}$alkyl-,
(5) hydrogen,
(6) primary amines, and
(7) secondary amines, and with the proviso that when $R_3$ is hydrogen, $R_6$ and $R_7$ may also form a (1) borylidene group,

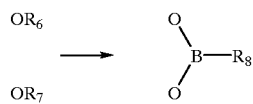

in which $R_8$ is a phenyl optionally substituted by one to five substituents, halogen or lower alkyl in any combination, or (2) $R_6$ and $R_7$ are both hydrogen, and wherein the dotted lines at x, y and z represent possible double bonds, when any are present, being either x and z in combination or x, y or z alone or none; or a corresponding stereoisomer thereof.

2. A compound according to claim 1, wherein independently $R_1$ is methyl, $R_2$ is methyl, $R_3$ is 2-methylbutyrate, $R_4$ is n-butyl, $R_5$ is selected form the group consisting of hydrogen, 1-methylpropyl and 1, 1-dimethylpropyl, $R_6$ and $R_7$ form to

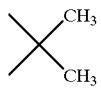

R8 is phenyl or parafluoro phenyl. and x and z are double bonds.

3. A compound of formula IV,

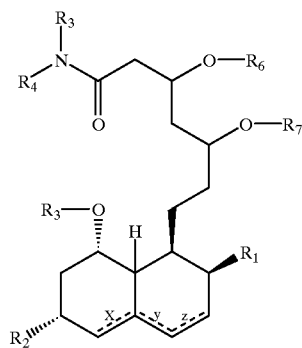

wherein $R_1$, $R_2$, $R_3$, $R_4$, $R_6$ and $R_7$ and x, y and z are defined as for a compound of formula II in claim 1, or a corresponding stereoisomer thereof, with the proviso that $R_3$ and $R_4$ are not hydrogen, and $R_6$ and $R_7$ may also form a borylidene group, as defined in claim 1.

4. A process for the preparation of a compound of formula II as defined in claim 1 comprising reacting a compound of formula I,

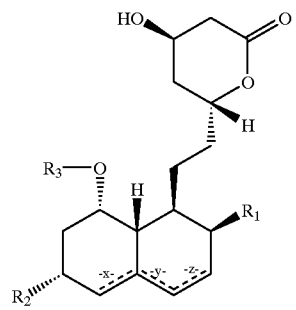

wherein $R_1$, $R_2$ and $R_3$ and x, y and z are defined as for a compound of formula II in claim 1, with the proviso that $R_3$ is not hydrogen and $R_1$, $R_2$, x, y and z are the same for the starting material and the end product, or a corresponding stereoisomer thereof, with a corresponding amine, followed by the protection of the hydroxyl groups formed upon opening of the lactone ring in the compound of formula I, by reaction with a protective group forming agent.

5. The process according to claim 4 wherein $R_3$ is 2-methylbutylrate in both formula I and formula II.

6. The process according to claim 4 or 5, wherein the amine is selected from the group consisting of:

(1) ammonia, (2) primary amines, and (3) secondary amines, and the protective group forming agent is selected from the group consisting( of:

(1) ketones, (2) aldehydes, (3) acetals, (4) sulfonyl chloride, followed by oxidation with sodium periodate, (5) phosphonyl chloride, followed by reaction with an alcohol, amine or water and (6) boronic acid.

7. A process for the preparation of a compound of formula II as defined in claim 1, with the proviso that $R_3$ is hydrogen, and wherein both $R_6$ and $R_7$ may also be hydrogen or a silyl protecting group, comprising reacting a compound of formula II as defined in claim 1, with the proviso that $R_3$ is not hydrogen, and wherein both R6 and R7 may also be hydrogen or a silyl protecting group or form a boiylidene moiety, and where all the parameters R, x, y and z are the same for the starting material and the end product except for $R_3$, with at least one suitable agent to remove the $R_3$ ester moiety.

8. The process according to claim 7 wherein the at least one agent is selected from the group consisting of:

(1) lithiumaluniliumhydride, (2) aluminiumhydride, (3) diisobutylaluminiumhydride (4) LiY and wherein Y is $C_{1-6}$alkyl or $C_{6-14}$aryl, and (5) ZMgCl, and (6) ZMgBr wherein Z is $C_{1-6}$alkyl or $C_{6-14}$aryl.

9. A process for the preparation of a compound of formula II as defined in claim 1, with the proviso that $R_3$ is hydrogen, and wherein both $R_6$ and $R_7$ may also be hydrogen or a silyl protecting group, comprising reacting a compound of formula II as defined in claim 1, with the proviso that $R_3$ is not hydrogen, and wherein both $R_6$ and $R_7$ may also be hydrogen or a silyl protecting group or form a boiylidene moiety, and where R, x, y and z are the same for the starting[ ] material and the end product except for $R_3$, with a primary amine of the formula $R_4NH_2$ with $R_4$ as defined in claim 1, with the proviso that $R_4$ is not part of a heterocycle moiety.

10. A process for the preparation of a compound of formula II as defined in claim 1, with the proviso that $R_3$, $R_5$, $R_6$ and $R_7$ are hydrogen, and $R_1$, $R_2$, x, y and z are the same for the starting material and the endproduct, comprising reacting a compound of formula I as defined in claim 4, with an excess of a primary amine of the formula $R_4NH_2$ as defined in claim 9 at a temperature between about 1000° C. and 250° C.

11. A process for the preparation of a compound of formula IV as defined in claim 3, comprising the step of reacting a compound of formula III, or the corresponding stereoisomer thereof,

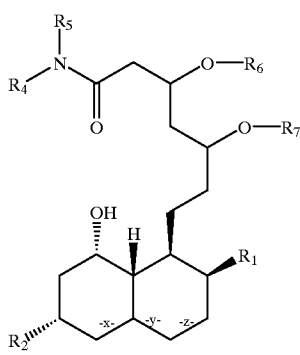

(III)

wherein $R_1$, $R_2$, $R_4$, R6, and $R_7$ are as defined for formula II in claim 5, and $R_5$ is hydrogen, and with the proviso that $R_6$ and $R_5$ are not hydrogen, and where R, x, y and z are the same for the starting material and the end product, with a suitable corresponding acylation agent.

12. A process for the preparation of a compound of formula II as defined in claim 1, with the proviso that $R_3$, $R_5$, $R_6$, $R_7$ are not hydrogen, comprising the step of reacting a compound of formula II wherein $R_1$, $R_2$, $R_4$, $R_5$, $R_6$ and $R_7$ are as defined in claim 1 and $R_3$ is hydrogen, with the proviso that $R_5$, $R_6$ and $R_7$ are not hydrogen, and where R, x, y and z are the same the for starting material and the end product except for $R_3$, with a suitable corresponding acylation agent.

13. The process according to claim 8 or 9 wherein the acylation agent is selected form the group consisting of:
(1) acid chloride of the corresponding acyl group,
(2) free acid of the corresponding acyl group, and
(3) acid anhydride of the corresponding acyl group.

14. A process for the preparation of the compound of formula I as defined in claim 4, from a compound of formula I as defined in claim 4, with the proviso that the $R_3$ moiety of the compound as prepared may be different from the $R_3$ moiety of the starting compound and where the other parameters are the same for starting material and end product, comprising the following steps:
a) ring opening of the lactone by formation of an amide bond and forming a protective group according to claim 4,
b) reduction of the $R_3$ moiety of formula II according to claim 7, c) acylation of the compound of formula III according to claim 11 or a compound of formula II according to claim 12,
d) removal of the acetal moiety and hydrolysis of the amide group of formula IV as defined in claim 3, or of a compound of formula II as defined in claim 1, into formula V, wherein M forms any pharmaceutically acceptable salt, acid or ester, and
e) lactonization of formula V into formula I by heating.

15. A process for the preparation of the compound of formula I as defined in claim 4, from a compound of formula I as defined in claim 4, with the proviso that tile $R_3$ moiety of the compound as prepared may be different from the $R_3$ moiety of the starting compound and where the other parameters are the same for the starting material and the end product, comprising the following steps:
a) reacting the compound of formula I with an amine $R_4NH_2$ as defined in claim 9,
b) formation of a protective group according to claim 4,
c) acylation of the compound of formula III according to claim II or a compound of formula 11 according to claim 12,
d) removal of the acetal moiety and hydrolysis of the amide groups of formula IV as defined in claim 3, or of a compound of formula II as defined in claim 1, into formula V, wherein M forms any pharmaceutically acceptable salt, acid or ester, and
e) lactonization of formula V into formula I by heating.

16. A process to prepare simvastatin from lovastatin according to claim 12, comprising the following steps:
a) ring opening of the lactone of lovastatin by formation of an amide bond with n-butylamine, followed by dioxane forming with acetone or dimethoxypropane;
b) removal of the 2-methylbutyrate ester group of the compound formed in step a) by reaction with an agent selected from the group consisting of,
(1) lithiumaluminumhydride,
(2) aluminiumhydride,
(3) diisobutylaluminiumhydride,
(4) LiY and wherein Y is $C_{1-6}$alkyl or $C_{5-14}$aryl,
(5) ZMgCl, and
(6) ZMgBr wherein Z is $C_{1-6}$alkyl or $C_{6-14}$aryl;
c) acylation of the compound formed in step b) by reaction with 2,2-dimethylbutyl chloride in the presence of para-toluene sulphonic acid, hydrogen chloride or sulfuric acid;
d) removal of the dioxane moiety and of the amide group of the compound formed in step c) by hydrolysis, optionally followed by reaction with ammonium hydroxide to form ammonium salt of simvastatin and
e) lactonization of the ammonium salt or sodium salt of simvastatin or by heating in toluene to form simvastatin, followed by crystallization.

17. A process to prepare simvastatin from lovastatin, comprising the following steps:
a) ring opening of the lactone of lovastatin, by formation of an amide bond with n-butylamine, followed by dioxane forming with acetone or dimethoxypropane,
b) α-methylation of the 2-methylbutyrate side chain of the compound formed in step a) with methyl iodide,
c) removal of the dioxane moiety and of the amide group of the compound formed in step a) by hydrolysis, optionally followed by reaction with ammonium hydroxide to form ammonium salt of simvastatin, d) lactonization of the ammonium salt or sodium salt of simvastatin or by heating in toluene to form simvastatin, followed by crystallization.

18. A process for preparing simvastatin according to claim 16 or 17 from a crude lovastatin, which contains no more than about 30% of impurities.

19. The compound of claim 1, wherein the 5, 6 or 7 membered heterocyclic moiety is selected from the group consisting of pyrrolidine, piperidine and a homopiperidine.

20. The compound of claim 1, wherein $R_{12}$ is a primary amine when $R_6$ and $R_7$ form a cyclic phosphate.

21. The compound of claim 20, wherein said primary amine is selected from the group consisting of cyclohexylamine and n-butylamine.

22. The compound of claim 1, wherein $R_8$ is selected from the group consisting of phenyl and para-fluorophenyl when $R_6$ and $R_7$ form a borylidene group.

23. The process of claim 4, wherein said reaction with a protective group forming agent takes place in the presence of at least one catalytic agent.

24. The process of claim 23, wherein said at least one catalytic agent is selected from the group consisting of para-toluene sulfonic acid and sulfuric acid.

25. A process for the preparation of a compound of formula II as defined in claim wherein $R_1$ is methyl; $R_2$ is hydrogen or methyl; $R_3$ is 2-methylbutyryl; $R_4$ is $C_{1-15}$ straight or branched alkyl; $R_5$ is hydrogen; $R_6$ and $R_7$ are as defined in claim 1 with the proviso that both $R_6$ and $R_7$ are not hydrogen; and, x and z are both double bonds; comprising reacting a compound of formula 11 wherein $R_1$, $R_2$, $R_3$, $R_4$, $R_5$, x and z are as defined above, and $R_6$ and $R_7$ are both hydrogen with a protective group forming agent.

26. The process of claim 25 wherein the protective group forming agent is selected from the group consisting of:

(1) ketones, (2) aldehydes, (3) acetals, (4) sulfonyl chloride, followed by oxidation with sodium periodate, (5) phosphonyl chloride, followed by reaction with an alcohol, amine or water, and (6) boronic acid.

27. The process of claim 26, wherein said reaction with a protective group forming agent takes place in the presence of at least one catalytic agent.

28. The process of claim 27, wherein said at least one catalytic agent is selected from the group consisting of para-toluene sulfonic acid and sulfuric acid.

29. The process of claim 6, wherein $R_1$ is methyl and $R_2$ is hydrogen or methyl in both formulas I and II, and wherein $R_4$ is straight or branched $C_{1-15}$ alkyl, $R_5$ is hydrogen, $R_6$ and $R_7$ are as defined in claim 1, with the proviso that $R_6$ and $R_7$ are not both hydrogen, and x and z are double bonds.

30. The process of claim 29 wherein $R_2$ is methyl.

31. The process of claim 30 wherein $R_4$ is n-butyl or cyclohexyl.

32. The process of claim 31 wherein $R_4$ is n-butyl.

33. The process of claim 6, wherein the protective group forming agent is acetone.

34. The process of claim 7, wherein both $R_6$ and $R_7$ are t-butyl dimethyl silyl.

35. The process of claim 8, wherein the agent is LiY and Y is n-butyl.

36. The process of claim 8, wherein the agent is ZMgCl and Z is methyl.

37. The process of claim 8, wherein the reducing agent is ZMgBr and Z is methyl.

38. The process of claim 9, wherein both $R_6$, and $R_7$ are t-butyl dimethyl silyl.

39. A compound of formula II as defined in claim 1 wherein $R_1$ is methyl; $R_2$ is hydrogen or methyl; $R_3$ is 2-methylbutyryl; $R_4$ is $C_{1-15}$ straight or branched alkyl; $R_5$ is hydrogen; $R_6$ and $R_7$ are as defined in claim 1; and, x and z are both double bonds.

40. The compound of claim 39 wherein $R_6$ and $R_7$ are both hydrogen.

41. The compound of claim 39 wherein $R_6$ and $R_7$ are not both hydrogen.

* * * * *

UNITED STATES PATENT AND TRADEMARK OFFICE
CERTIFICATE OF CORRECTION

PATENT NO. : 6,294,680 B1
DATED : September 25, 2001
INVENTOR(S) : Vries et al.

Figure 2:
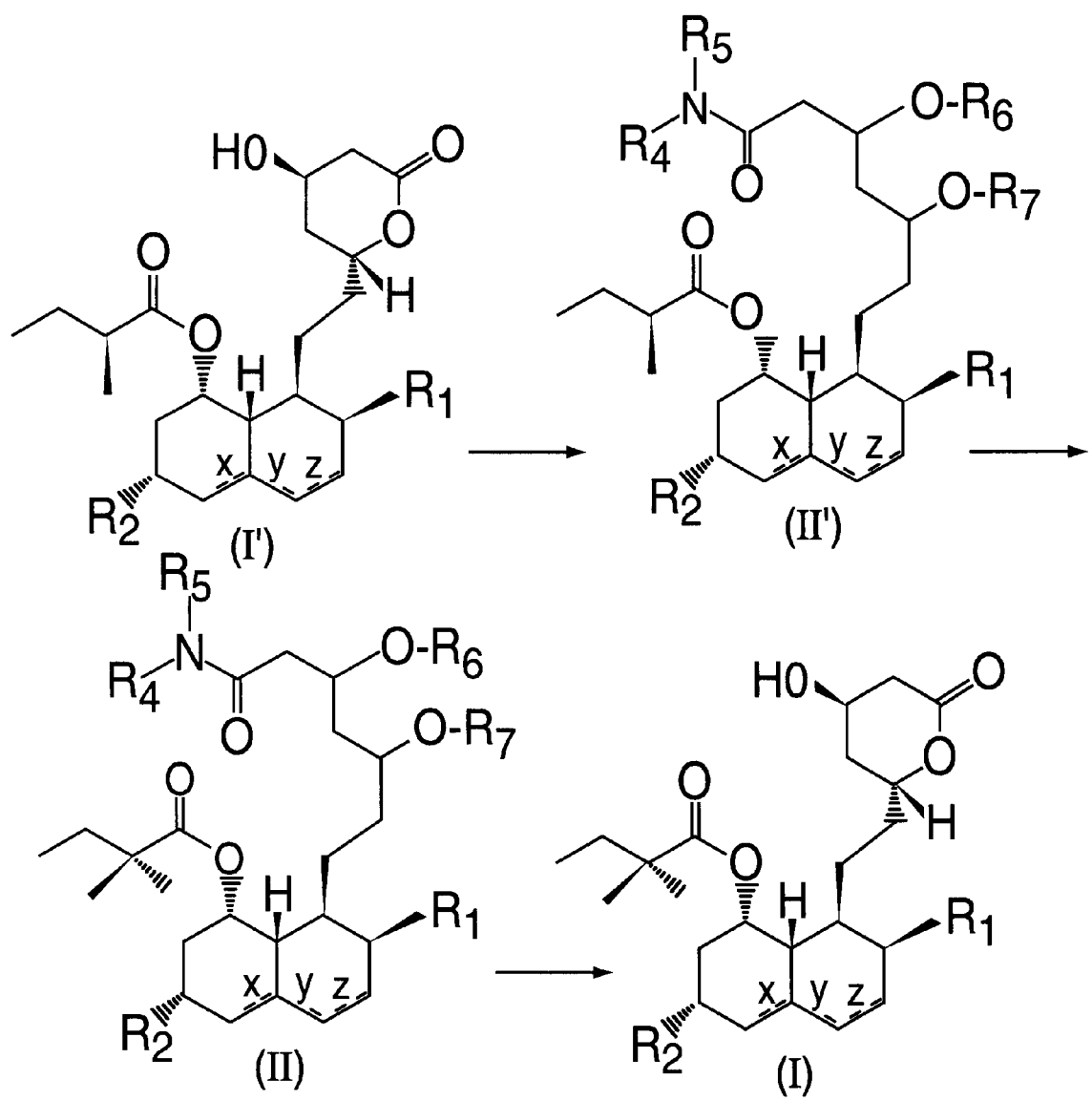
FIG. 2 is a schematic of the process for preparing semi-synthetic statins, depicted as formula I, by applying direct α-methylation on the ester moiety of a compound of formula II'.

It is certified that error appears in the above-identified patent and that said Letters Patent is hereby corrected as shown below:

Column 1,
Line 33, change "U.S:" to -- U.S. --;
Line 41, change "boronic acid" to -- boric acid --;

Column 2,
Line 60, change "" to -- $R_1$ --;
Line 60, change "wherein R and $R_2$" to -- wherein $R_1$ and $R_2$ --;

Column 4,
Line 38, change "lithiumaluminumhydride" to -- lithium aluminum hydride --;
Lines 38-39, change "methylmagnesiumchloride" to -- methyl magnesium chloride --;
Line 39, change "n-butyllithium" to -- n-butyl lithium --;
Lines 61, 65 and 66, change "figure I" to -- figure 1 --;

Column 6,
Line 32, change "n-butyllithium" to -- n-butyl lithium --;
Line 44, change "Figure I" to -- Figure 1 --;
Line 53, change "1,3 dicyclohexylcarbodiimide" to -- 1,3 dicyclohexyl carbodiimide --;
Line 57, change "4-dimethylaminopyridine" to -- 4-dimethyl aminopyridine --;
Line 58, change "1 10° C.," to -- 110° C., --;

Column 7,
Line 25, change "R6" to -- $R_6$ --;
Line 41, change "$R_3$Pwhere" to -- $R_3$P where --;

Column 8,
Line 9, change "(lineair)" to -- (linear) --;
Line 54, change "Butilamide" with -- Butylamide --;
Line 55, change "Thionyichloride" to -- Thionylchloride --;

Column 9,
Line 10, change "FIG. II" to -- FIG. 2 --;
Line 29, change "Me1" to -- Mel --;

UNITED STATES PATENT AND TRADEMARK OFFICE
CERTIFICATE OF CORRECTION

PATENT NO. : 6,294,680 B1
DATED : September 25, 2001
INVENTOR(S) : Vries et al.

It is certified that error appears in the above-identified patent and that said Letters Patent is hereby corrected as shown below:

Column 10,
Line 15, change "n-butyllithium" to -- n-butyl lithium --;
Line 20, change "4-dimethylaminopyridine" to -- 4-dimethyl aminopyridine --;
Line 23, change "2,2-Dimethylbutyric" to -- 2,2-Dimethyl butyric --;
Line 26, change "of ml" to -- ml of --;
Line 43, change "NH4OH" to -- $NH_4OH$ --;

Column 11,
Line 11, change "Lithium" to -- lithium --;

Column 12,
Line 58, change "N,N-dimethylaminopyridine" to -- N,N-dimethyl aminopyridine --;
Line 59, change "2,2-dimethylbutyric" to -- 2,2-dimethyl butyric --;

Column 13,
Line 37, change "$R_f$:9.$^{27}$." to -- $R_f$:9.27. --;
Line 42, change "2,2-dimethylbutyryl" to -- 2,2-dimethyl butyryl --;
Line 46, change "(R:" to -- $R_1$: --;

Column 14,
Line 28, change "Pyrrolidin" to -- Pyrrolidine --;
Line 43, change "cased" to -- ceased --;
Line 43, change "($Na_2SO_4$" to -- $Na_2SO_4$ --;

Column 16,
Line 7, change "C1-6alkyl," to -- $C_{1-6}$alkyl, --;

Column 17,
Formula IV, change "$R_3$" to -- $R_5$ --;
Line 23, change "to" to -- together --;
Line 34, change "R8" to -- $R_8$ --;
Line 41, change "$R_3$" to -- $R_5$ --;

UNITED STATES PATENT AND TRADEMARK OFFICE
CERTIFICATE OF CORRECTION

PATENT NO.    : 6,294,680 B1
DATED         : September 25, 2001
INVENTOR(S)   : Vries et al.

It is certified that error appears in the above-identified patent and that said Letters Patent is hereby corrected as shown below:

Column 18,
Line 34, change "consisting(" to -- consisting --;
Line 51, change "boiylidene" to -- borylidene --;
Line 57, change "lithiumaluniliumhydride" to -- lithium alunilium hydride --;
Line 58, change "aluminiumhydride" to -- aluminium hydride --;

Column 19,
Line 3, change "boiylidene" to -- borylidene --;
Line 4, remove "[ ]";
Line 5, change "$R_{3+}$" to -- $R_3$ --;
Line 14, change "1000° C." to -- 100° C. --;
Line 36, change "R6," to -- $R_6$ --;
Line 47, change "the for" to -- for the --;

Column 20,
Line 12, change "tile" to -- the --;
Line 22, change "II" to -- 11 --;
Line 22, change "11" to -- II --;
Line 39, change "lithiumaluminumhydride," to -- lithium aluminum hydride, --;
Line 40, change "aluminiumhydride," to -- aluminium hydride --;
Line 41, change "diisobutylaluminiumhydride," to -- diisobutyl aluminium hydride --;

Column 21,
Line 25, change "claim wherein" to -- claim 1 wherein --;

Signed and Sealed this

Twenty-second Day of July, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,294,680 B1
DATED         : September 25, 2001
INVENTOR(S)   : Vries et al.

It is certified that error appears in the above-identified patent and that said Letters Patent is hereby corrected as shown below:

Column 1,
Line 33, change "U.S:" to -- U.S. --;
Line 41, change "boronic acid" to -- boric acid --;

Column 2,
Line 60, change "" to -- $R_1$ --;
Line 60, change "wherein R and $R_2$" to -- wherein $R_1$ and $R_2$ --;

Column 4,
Line 38, change "lithiumaluminumhydride" to -- lithium aluminum hydride --;
Lines 38-39, change "methylmagnesiumchloride" to -- methyl magnesium chloride --;
Line 39, change "n-butyllithium" to -- n-butyl lithium --;
Lines 61, 65 and 66, change "figure I" to -- figure 1 --;

Column 6,
Line 32, change "n-butyllithium" to -- n-butyl lithium --;
Line 44, change "Figure I" to -- Figure 1 --;
Line 53, change "1,3 dicyclohexylcarbodiimide" to -- 1,3 dicyclohexyl carbodiimide --;
Line 57, change "4-dimethylaminopyridine" to -- 4-dimethyl aminopyridine --;
Line 58, change "1 10° C.," to -- 110° C., --;

Column 7,
Line 25, change "R6" to -- $R_6$ --;
Line 41, change "$R_3$Pwhere" to -- $R_3$P where --;

Column 8,
Line 9, change "(lineair)" to -- (linear) --;
Line 54, change "Butilamide" with -- Butylamide --;
Line 55, change "Thionyichloride" to -- Thionylchloride --;

Column 9,
Line 10, change "FIG. II" to -- FIG. 2 --;
Line 29, change "Me1" to -- MeI --;

UNITED STATES PATENT AND TRADEMARK OFFICE
CERTIFICATE OF CORRECTION

PATENT NO. : 6,294,680 B1
DATED : September 25, 2001
INVENTOR(S) : Vries et al.

It is certified that error appears in the above-identified patent and that said Letters Patent is hereby corrected as shown below:

Column 10,
Line 15, change "n-butyllithium" to -- n-butyl lithium --;
Line 20, change "4-dimethylaminopyridine" to -- 4-dimethyl aminopyridine --;
Line 23, change "2,2-Dimethylbutyric" to -- 2,2-Dimethyl butyric --;
Line 26, change "of ml" to -- ml of --;
Line 43, change "NH4OH" to -- $NH_4OH$ --;

Column 11,
Line 11, change "Lithium" to -- lithium --;

Column 12,
Line 58, change "N,N-dimethylaminopyridine" to -- N,N-dimethyl aminopyridine --;
Line 59, change "2,2-dimethylbutyric" to -- 2,2-dimethyl butyric --;

Column 13,
Line 37, change "$R_f:9.^{27}$." to -- $R_f:9.27$. --;
Line 42, change "2,2-dimethylbutyryl" to -- 2,2-dimethyl butyryl --;
Line 46, change "(R:" to -- $R_1$: --;

Column 14,
Line 28, change "Pyrrolidin" to -- Pyrrolidine --;
Line 43, change "cased" to -- ceased --;
Line 43, change "($Na_2SO_4$" to -- $Na_2SO_4$ --;

Column 16,
Line 7, change "C1-6alkyl," to -- $C_{1-6}$alkyl, --;

Column 17,
Formula IV, change "$R_3$" to -- $R_5$ --;
Line 23, change "to" to -- together --;
Line 34, change "R8" to -- $R_8$ --;
Line 41, change "$R_3$" to -- $R_5$ --;

UNITED STATES PATENT AND TRADEMARK OFFICE
CERTIFICATE OF CORRECTION

PATENT NO.    : 6,294,680 B1
DATED         : September 25, 2001
INVENTOR(S)   : Vries et al.

It is certified that error appears in the above-identified patent and that said Letters Patent is hereby corrected as shown below:

Column 18,
Line 34, change "consisting(" to -- consisting --;
Line 50, change "R6 and R7" to -- $R_6$ and $R_7$ --;
Line 51, change "boiylidene" to -- borylidene --;
Line 57, change "lithiumaluniliumhydride" to -- lithium alunilium hydride --;
Line 58, change "aluminiumhydride" to -- aluminium hydride --;

Column 19,
Line 3, change "boiylidene" to -- borylidene --;
Line 4, remove "[ ]";
Line 5, change "$R_{3+}$" to -- $R_3$ --;
Line 14, change "1000° C." to -- 100° C. --;
Line 36, change "R6," to -- $R_6$ --;
Line 47, change "the for" to -- for the --;

Column 20,
Line 12, change "tile" to -- the --;
Line 22, change "II" to -- 11 --;
Line 22, change "11" to -- II --;
Line 39, change "lithiumaluminumhydride," to -- lithium aluminum hydride, --;
Line 40, change "aluminiumhydride," to -- aluminium hydride --;
Line 41, change "diisobutylaluminiumhydride," to -- diisobutyl aluminium hydride --;

UNITED STATES PATENT AND TRADEMARK OFFICE
CERTIFICATE OF CORRECTION

PATENT NO.    : 6,294,680 B1
DATED         : September 25, 2001
INVENTOR(S)   : Vries et al.

It is certified that error appears in the above-identified patent and that said Letters Patent is hereby corrected as shown below:

Column 21,
Line 25, change "claim wherein" to -- claim 1 wherein --;

This certificate supersedes Certificate of Correction issued July 22, 2003.

Signed and Sealed this

Twenty-Sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,294,680 B1 Page 1 of 1
DATED : September 25, 2001
INVENTOR(S) : Tn Rene Vries et al.

It is certified that error appears in the above-identified patent and that said Letters Patent is hereby corrected as shown below:

Column 19,
Line 14, replace "about 1000° C." to -- about 100° C. --;

Signed and Sealed this

Twenty-eighth Day of December, 2004

JON W. DUDAS
*Director of the United States Patent and Trademark Office*